United States Patent [19]

Newyear

[11] 3,956,176

[45] May 11, 1976

[54] CATALYST FOR PREPARATION OF TETRAMETHYL LEAD IN REACTION OF METHYL HALIDE AND SODIUM-LEAD ALLOY

[75] Inventor: Edward G. Newyear, Corpus Christi, Tex.

[73] Assignee: PPG Industries, Inc., Pittsburgh, Pa.

[22] Filed: Aug. 26, 1971

[21] Appl. No.: 175,339

Related U.S. Application Data

[62] Division of Ser. No. 22,693, March 25, 1970, Pat. No. 3,642,849.

[52] U.S. Cl............................ 252/426; 260/437 R
[51] Int. Cl.$^2$......................................... B01J 31/02
[58] Field of Search................. 252/426; 260/615 B

[56] References Cited
UNITED STATES PATENTS

| | | | |
|---|---|---|---|
| 3,281,442 | 10/1966 | Pedrotti et al. | 260/437 R |
| 3,401,188 | 9/1968 | Sandy | 260/437 R |
| 3,401,189 | 9/1968 | Sandy et al. | 260/437 R |
| 3,450,608 | 6/1969 | Craig | 260/615 B |

OTHER PUBLICATIONS

Cretcher et al., "Syntheses With $\beta$, $\beta'$-Dichloro–Diethyl Ether," JACS 47, pp. 163–164 (1925).

Primary Examiner—Patrick P. Garvin
Attorney, Agent, or Firm—Irwin M. Stein; John E. Curley

[57] ABSTRACT

A method of preparing tetramethyllead utilizing a novel catalyst consisting of methanol and diglyme with or without anthracene is described. The catalyst is used in quantities of at least 0.02 moles of methanol and diglyme per mole of sodium-lead alloy employed. Catalyst compositions, one comprising 2.55 to 68.28 weight per cent methanol, 5.22 to 92.72 per cent diglyme and 3.56 to 77.08 per cent anthracene and a second one comprising 30 to 10 per cent methanol and 70 to 90 per cent diglyme basis the mixture, are claimed.

2 Claims, No Drawings

CATALYST FOR PREPARATION OF TETRAMETHYL LEAD IN REACTION OF METHYL HALIDE AND SODIUM-LEAD ALLOY

CROSS-REFERENCE TO RELATED APPLICATIONS

This application is a division of application Ser. No. 22,693, filed Mar. 25, 1970 now issued as U.S. Pat. 3,642,849.

BACKGROUND OF THE INVENTION

Gasoline formulations have in recent years often included significant quantities of tetramethyllead as an antiknock agent. Tetramethyllead, unlike tetraethyllead, is produced from methyl halide and sodium-lead alloy only with considerable difficulty and normally requires the presence of a catalyst in the reaction zone. Thus, U.S. patents such as U.S. Pat. Nos. 3,048,610; 3,192,420 and 3,401,188 and British Patent No. 1,015,268 all describe various processes for the manufacture of tetramethyllead from sodium-lead alloy and methyl halide utilizing various catalyst systems.

While the catalyst systems described in the prior art are efficacious in the production of tetramethyllead in satisfactory quantities, drawbacks are encountered in the utilization of most of them. Thus, various aluminum containing catalysts described in the prior art are found to be somewhat difficult to handle in that they are subject to spontaneous ignition. The utilization of other catalysts such as ammonia in the presence of small quantities of monohydroxylic compounds, as described in the aforementioned British patent, requires sophisticated equipment in order to avoid leaks during reaction. Therefore, while tetramethyllead is capable of being produced in accordance with the various catalyst systems described in the prior art, some of the disadvantages inherent in these prior art catalyst systems are not easily overcome.

THE PRESENT INVENTION

In accordance with the present invention a catalyst system which is safe, easy to handle, and which requires no special equipment other than that conventionally employed in present commercial plants for the production of tetramethyllead is utilized to manufacture tetramethyllead from methyl halide and sodium-lead alloy in satisfactory yields. Thus, in accordance with the present invention, sodium-lead alloy and methyl halide, preferably as methyl chloride, are reacted in a pressure vessel in the presence of a catalyst comprising methanol and diglyme in quantities of at least 0.020 mole of catalyst per mole of sodium-lead alloy present in the reactor.

In a further embodiment of the instant invention a catalyst system comprising methanol, diglyme and anthracene is employed to produce tetramethyllead from methyl halide and sodium-lead alloy. The anthracene in this system is present in a quantity of between about 3.56 and about 77.08 percent by weight of the mixture. The preferred embodiment of the latter catalyst system consists essentially of diglyme (3.3 to 92.72 percent), methanol (2.55 to 68.28 percent) and anthracene (3.56 to 77.08 percent).

In carrying out the instant invention, recourse to the utilization of conventional autoclaves now employed in the tetramethyllead industry may be had. Thus, autoclaves capable of withstanding pressures of 100 to 600 psig or more are typically employed.

Temperatures at which the reaction may be carried out may vary. In general, reaction temperatures are from −20°C. to 150°C. Preferably the temperatures utilized are in the range of 60° to 130°C.

The methyl halide, utilized as a methylating agent in accordance with the instant invention, is typically methyl chloride; however, the use of other methyl halides is contemplated. The quantity of methylating agent employed normally ranges between 1 mole to 10 moles of methyl halide per mole of sodium-lead alloy used. Preferably, from above 1 to about 4 to about 8 moles of methyl halide per mole of sodium-lead alloy is used.

Sodium-lead alloy utilized in the instant process is typically a monosodium-lead alloy containing 50 mole percent sodium and 50 mole percent lead. While a monosodium-lead alloy is preferred in the operation of the instant invention, recourse to sodium-lead alloys having varying molar ratios of sodium to lead may be utilized.

Monosodium-lead alloy as typically used is screened to a −¼ inch to 40 mesh size, though any conventional sodiumlead alloy particle size may be used if desired.

When ternary mixtures are used for catalyst in the instant invention there is present in the final mixture at least 0.026 mole of diglyme and methanol per mole of the alloy. The anthracene in such instance is utilized in smaller quantities, typically between 0.001 to 0.1 mole per mole of lead alloy. Preferably anthracene, when employed in the catalyst, is used in quantities ranging between 0.005 to 0.05 mole.

The novel catalyst compositions of the instant invention include anthracene, diglyme and methanol containing on a weight basis, 3.56 to 77.08 weight percent anthracene, 5.22 to 92.72 weight percent diglyme and 2.55 to 62.28 weight percent methanol basis the alloy fed in the reaction. The novel catalyst compositions contemplated also include diglyme and methanol containing on a weight basis 70 to 90 weight percent diglyme and 30 to 10 weight percent methanol.

In utilizing diglyme and methanol catalyst compositions without any anthracene present to produce tetramethyllead from sodium-lead alloy and methyl halide, the quantities of diglyme and methanol employed are generally in the range of between 0.01 mole of diglyme to 0.2 mole of diglyme per mole of sodium-lead alloy and between 0.01 mole of methanol to 0.2 mole of methanol per mole of sodium-lead alloy. In general the combination of diglyme and methanol is utilized in quantitites of at least about 0.2 mole per mole of sodium-lead alloy and preferably, between 0.3 to 0.5 mole per mole of sodium-lead alloy employed. The compositions of diglyme, methanol and anthracene typically contain 2.55 to 68.28 percent by weight methanol, 5.22 to 92.72 percent by weight diglyme and 3.56 to 77.08 percent by weight anthracene basis the mixture.

For a more complete understanding of the instant invention, reference is made to the following examples:

EXAMPLE I

A series of experiments were run utilizing anthracene, diglyme and methanol in a reaction system containing 0.2 mole of sodium-lead alloy and different quantities of methyl chloride. These runs were made in a stainless steel laboratory autoclave at a reaction temperature of 120°C. ±3°C. and with a total reaction time of 2 hours. During the course of the experiment, several runs were made in which the quantities of diglyme, anthracene and methanol were varied considerably. Table 1 shows the composition of the catalyst for 11 experiments conducted to produce tetramethyllead utilizing this novel catalyst system and the results obtained.

the tetramethyllead yield obtained during the runs are shown below in Table 2:

Table 2

| Run No. | Mole of Material Per Mole of Alloy Used | | | | % Sodium Reacted | % TML Yield (Based on Na Charged) | |
|---|---|---|---|---|---|---|---|
| | Anthracene | Diglyme | Methanol | Methyl Chloride | | By G.C.* | By EDTA** |
| 1 | 0.030 | 0.0 | 0.075 | 7.35 | 14.6 | 3.3 | 2.1 |
| 2 | 0.030 | 0.090 | 0.0 | 7.20 | 1.5 | 1.5 | 1.0 |
| 3 | 0.030 | 0.160 | 0.085 | 7.20 | 100 | 48.7 | 52.6 |
| 4 | 0.0 | 0.085 | 0.080 | 7.65 | 54.6 | 29.7 | 32.2 |
| 5 | 0.030 | 0.065 | 0.165 | 6.60 | 65.0 | 32.6 | 36.3 |
| 6 | 0.055 | 0.090 | 0.085 | 6.95 | 66.8 | 42.9 | 45.3 |

*G.C. — Analysis by gas chromatograph.
**EDTA — Analysis by ethylenediaminetetraacetic acid titration.

Table 1

| Run No. | Catalyst Composition Moles Per Mole of Alloy | | | Reacted | % Tetramethyllead | | Methyl Chloride Moles per Moles of Alloy |
|---|---|---|---|---|---|---|---|
| | Anthracene | Diglyme | Methanol | | By G.C.* | By EDTA** | |
| 1 | 0.005 | 0.145 | 0.145 | 68.3 | 39.2 | 38.9 | 6.20 |
| 2 | 0.005 | 0.130 | 0.015 | 10.7 | 19.3 | 14.4 | 6.65 |
| 3 | 0.030 | 0.080 | 0.075 | 21.8 | 29.6 | 27.2 | 7.00 |
| 4 | 0.050 | 0.015 | 0.020 | 11.5 | 12.1 | 7.3 | 7.05 |
| 5 | 0.005 | 0.010 | 0.025 | 3.2 | 0.7 | 4.1 | 6.90 |
| 6 | 0.030 | 0.085 | 0.065 | 21.6 | 35.3 | 34.6 | 6.70 |
| 7 | 0.050 | 0.145 | 0.025 | 25.2 | 18.1 | 18.0 | 6.70 |
| 8 | 0.005 | 0.010 | 0.150 | 37.3 | 12.6 | 12.2 | 6.10 |
| 9 | 0.050 | 0.145 | 0.155 | — | 39.2 | 36.6 | 7.00 |
| 10 | 0.030 | 0.080 | 0.085 | 66.6 | 39.8 | 36.3 | 7.20 |
| 11 | 0.050 | 0.075 | 0.040 | 41.3 | 25.7 | 26.6 | 6.90 |

*G.C. — Analysis by gas chromatograph.
**EDTA — Analysis by ethylenediaminetetraacetic acid titration.

EXAMPLE II

A further set of experiments were undertaken in the same laboratory stainless steel autoclave to produce tetramethyllead using diglyme-methanol with and without anthracene catalyst with methyl chloride and sodium-lead alloy. A reaction temperature of 120°C. ± 3°c. was employed in these runs and a reaction time of 2 hours was also used in all runs. 0.2 mole of sodiumlead alloy was employed in the reaction mass with varying quantities of methyl chloride. The concentration of the catalyst materials utilized, the methyl chloride concentration in the reaction, the percent sodium reacted, and

EXAMPLE III

A further set of runs were made utilizing 0.2 mole of ¼ to 40 mesh flakes of sodium-lead alloy and various quantities of methyl chloride. In these runs the catalyst system anthracene, methanol and diglyme was utilized as well as the catalyst system methanol and diglyme. The runs were made at a reaction time of 2 hours and at a temperature of 120°C. ± 4°C. Tetramethyllead yields of these runs on the basis of the sodium charged are shown below in Table 3:

Table 3

| Run No. | Mole per Mole of NaPb | | | | % Sodium Reacted | % TML Yield (Based on Na Charged) Experimental | |
|---|---|---|---|---|---|---|---|
| | Methyl Chloride | Anthracene | Methanol | Diglyme | | By G.C.* | By EDTA** |
| 1 | 7.70 | 0.044 | 0.13 | 0.15 | 77 | 54 | 46 |
| 2 | 6.25 | 0.055 | 0.16 | 0.0 | 36 | 5 | 5 |
| 3 | 7.90 | 0.044 | 0.0 | 0.12 | 4 | Trace | 1 |
| 4 | 6.50 | 0.055 | 0.14 | 0.12 | 75 | 41 | 42 |
| 5 | 6.80 | 0.044 | 0.13 | 0.15 | 75 | 41 | 40 |
| 6 | 6.40 | 0.0 | 0.15 | 0.15 | 72 | 37 | 35 |
| 7 | 6.85 | 0.0 | 0.16 | 0.15 | 82 | 46 | 46 |
| 8 | 7.35 | 0.050 | 0.11 | 0.14 | 93 | 40 | 43 |
| 9 | 6.70 | 0.050 | 0.05 | 0.15 | 52 | 34 | 34 |
| 10 | 7.25 | 0.0 | 0.16 | 0.15 | 76 | 45 | 44 |

*G.C. — Analysis by gas chromatograph.
**EDTA — Analysis by ethylenediaminetetraacetic acid titration.

As will be readily appreciated from the above runs, the catalyst system anthracene, methanol and diglyme is an effective catalyst system for the production of tetramethyllead. It is also readily seen from the above examples that when diglyme and methanol are utilized in the range stated hereinbefore, an effective tetramethyllead reaction takes place and tetramethyllead in appreciable quantities is produced. Since the catalyst system is easy to handle and not subject to some of the severe conditions typically associated with the handling of alkyl aluminum complex catalyst and gaseous catalyst heretofore employed in the prior art, an advantage is readily appreciated utilizing these catalyst systems for the manufacture of tetramethyllead.

While the invention had been described with reference to certain specific embodiments, it is not intended that it be so limited except insofar as appears in the accompanying claims.

I claim:

1. A catalyst composition consisting essentially of methanol, diglyme and anthracene.

2. The catalyst of claim 1 wherein the methanol is 2.55 to 68.28 percent by weight, diglyme is 5.22 to 92.72 percent by weight and anthracene is 3.56 to 77.08 percent by weight basis the composition.

* * * * *